United States Patent
Chu et al.

(10) Patent No.: US 7,478,571 B2
(45) Date of Patent: Jan. 20, 2009

(54) BALANCING MEANS FOR HIGH-SPEED SCANNING

(75) Inventors: Daniel Y. Chu, Hercules, CA (US); Paul J. Patt, Blackhawk, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 11/694,105

(22) Filed: Mar. 30, 2007

(65) Prior Publication Data

US 2007/0272878 A1    Nov. 29, 2007

Related U.S. Application Data

(60) Provisional application No. 60/790,068, filed on Apr. 7, 2006.

(51) Int. Cl.
*G01D 21/00* (2006.01)
(52) U.S. Cl. .................................................... 73/866.5
(58) Field of Classification Search ............. None
See application file for complete search history.

(56) References Cited

U.S. PATENT DOCUMENTS

| | | | | |
|---|---|---|---|---|
| 4,091,287 A | * | 5/1978 | Hounsfield | 378/19 |
| 4,401,890 A | * | 8/1983 | Blum | 250/363.05 |
| 5,501,114 A | * | 3/1996 | Okamoto et al. | 73/865.6 |
| 6,209,437 B1 | * | 4/2001 | Izvoztchikov et al. | 83/707 |
| 2007/0180914 A1 | * | 8/2007 | Kessler | 73/607 |

* cited by examiner

*Primary Examiner*—Robert R Raevis
(74) *Attorney, Agent, or Firm*—Townsend and Townsend and Crew; M. Henry Heines

(57) ABSTRACT

Translational motion of a scanning head relative to a planar target, or vice versa, is achieved by a belt and pulley system with a counterweight that is also driven by a belt and pulley system at the same speed but in the opposite direction as the scanning head. The components and belt and pulley system are oriented such that all moving components remain on one side of the target and remain so during their entire range of movement.

11 Claims, 4 Drawing Sheets

BALANCING MEANS FOR HIGH-SPEED SCANNING

CROSS-REFERENCE TO RELATED APPLICATION

This application claims the benefit of U.S. Provisional Patent Application No. 60/790,068, filed Apr. 7, 2006, the contents of which are incorporated herein by reference in their entirety.

BACKGROUND OF THE INVENTION

1. Field of the Invention

This invention relates to scanning systems used in procedures performed in real-time PCR or on microarrays of biological species such as nucleic acids or proteins, and for any type of procedure or analysis where very rapid illumination, observation, and/or detection are performed at a large number of individual sites arranged in a regular two-dimensional array.

2. Description of the Prior Art

Scanning systems to which this invention is addressed are mechanical conveyances that move a scanning head back and forth at a very rapid rate in a scanning pattern which consists of a line or a series of lines. Scanning systems have been designed for a variety of scanning heads, including those that emit or receive, or both emit and receive, light or other electromagnetic waves or particles, or acoustic signals. Data retrieved during the scan is typically sent to a signal processor for storage, recordation, comparison, and other common signal processing functions.

Targets that can be scanned by scanning systems include radiographic images, electronic packages and other electronic media, and multi-well plates containing arrays of biological samples. In all cases, the goals in effective scanning are high speed and positional accuracy. These goals tend to conflict with each other, however, since the movement of the scanning head requires rapid reversals in direction and rapid back and forth acceleration following the reversals. These accelerations and reversals create undesirable vibrations in the system, which give rise to measurement error and subject the system components to mechanical stresses that can lead to distortion and wear. These and other problems associated with scanning systems are disclosed in Ciechanski, F. J. (Sonoscan, Inc.), U.S. Pat. No. 4,781,067, issued Nov. 1, 1988; Kerr, R. S., et al. (Eastman Kodak Company), U. S. patent application Publication No. US 2005/0133749 A1, published Jun. 23, 2005; Kellerman, P. L., et al., U. S. patent application Publication No. US 2005/0254932 A1, published Nov. 17, 2005; Melville, C. D. (University of Washington), U.S. Pat. No. 5,995,264, issued Nov. 30, 1999; and Chubb, C. F. (Dynell Electronics Corp.), U.S. Pat. No. 3,541,561, issued Nov. 17 1970. The contents of these patents are hereby incorporated herein in their entirety.

SUMMARY OF THE INVENTION

The present invention resides in a counterbalanced scanning system in which the translational motion in the performance of the scanning is achieved by a belt and pulley system or any mechanical equivalent thereof, with a counterweight that is driven by the same belt and pulley system but arranged to travel in the direction opposite to the scanning direction. The invention encompasses systems in which the scanning head is moved by the belt and pulley system and the target is stationary, or the target is moved by the belt and pulley system and the scanning head is stationary, i.e., an inverse scanning operation. To encompass both options, the term "scanning pair" is used herein to refer to scanning head and the target, each referred to individually as "members" of the scanning pair. The member that is mounted to the belt and thereby moves with the rotation of the belt is termed a "mobile scanning pair member" while the other is termed a "stationary scanning pair member." The target to be scanned in this invention is a planar target, which is either a linear array of areas to be scanned or a two-dimensional array of such areas. Accordingly, when the scanning head is used as the mobile scanning pair member, the scanning head scans the target by traversing the target, and when the target is used as the mobile scanning pair member, the target passes over the scanning head. In each case, the mobile scanning pair member can be either above or below the stationary scanning pair member.

When the mobile scanning pair member is the scanning head, the counterweight can be a second scanning head of equal or approximately equal weight, which can be used in conjunction with the same planar target or a separate planar target. As for the belt and pulley system, they are referred to herein as "belt means" and they encompass embodiments in which both the mobile scanning pair member and the counterweight are on a single belt and embodiments in which each is mounted on a separate belt with the two belts driven by a common driving system to move in a coordinated manner. In all cases, the mobile scanning pair member and the counterweight move in synchronous linear motion, with one moving in a direction opposite to the other and at the same speed.

The orientation of the belt system relative to the target is such that all of the moving components, i.e., the mobile scanning pair member and the counterweight, remain on the same side of the target, as opposed to one being above the target and the other below. This is of particular advantage when the target is an array of biological samples. This is achieved in some embodiments by placing the mobile scanning pair member and counterweight on the same belt and arranging the axes of the belt pulleys to be parallel to the target plane, and by operating the system such that the motion of the mobile scanning pair member is restricted to a plane directly above the target plane and the motion of the counterweight is restricted to the plane above that of the mobile scanning pair member. In other embodiments, the mobile scanning pair member and counterweight are placed on separate belts with a common pulley system whose pulley axes are perpendicular to the target plane. The mobile scanning pair member and counterweight may both move within a common plane directly above the target plane, or one may be further distanced from the target plane than the other.

The term "scanning distance" is used to denote any distance between the two members of the scanning pair that will allow the scanning head to perform the scanning operation. For scanning heads that are emitters or receivers or light or other electromagnetic signal, the scanning distance is any distance through which the signal generated at one member of the scanning pair can be received by the other member.

The counterweight in all embodiments of the invention significantly reduces or eliminates vibrations in the scanning head caused by the rapid reversals in direction and accelerations.

DETAILED DESCRIPTION OF THE INVENTION AND PREFERRED EMBODIMENTS

Figure 1:
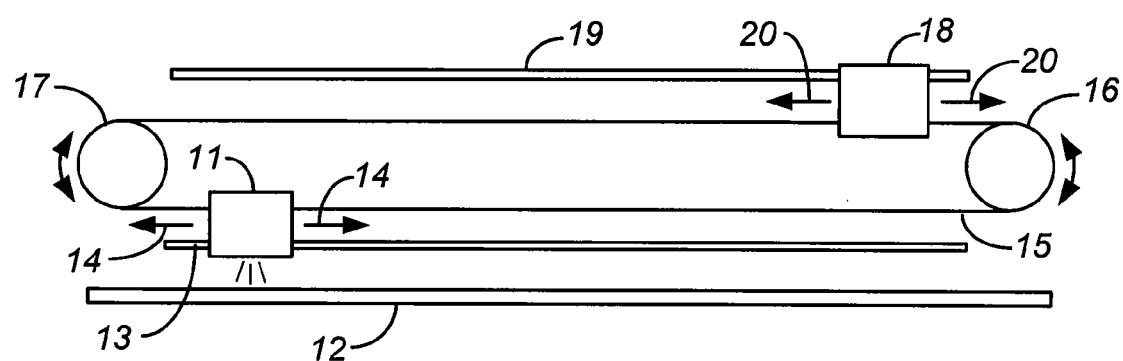
FIG. 1 is a side view of one example of a scanning system in accordance with the present invention.

While the features defining this invention are capable of implementation in a variety of constructions, the invention as a whole will be best understood by a detailed examination of specific embodiments. Some of these embodiments are shown in the drawings.

In the arrangement shown in FIG. 1, the scanning head 11 is positioned over a target plane 12 and slidably joined to a guide rail 13 above the target plane. To scan a line in the target plane 12, the scanning head 11 is moved along the rail 13 in the directions indicated by the arrows 14 by a belt 15 to which the scanning head 11 is affixed. The belt 15 is driven by a pulley system including a motorized driver pulley 16 and an idler pulley 17. A counterweight 18 is likewise affixed to the belt 15 and slidably joined to a second rail 19 to move in the direction indicated by the arrows 20. Because of its location on the belt 15, the counterweight 18 moves in the direction opposite to that of the scanning head 11, counterbalancing the inertial forces generated by the scanning head as the belt rotates.

Figure 2:
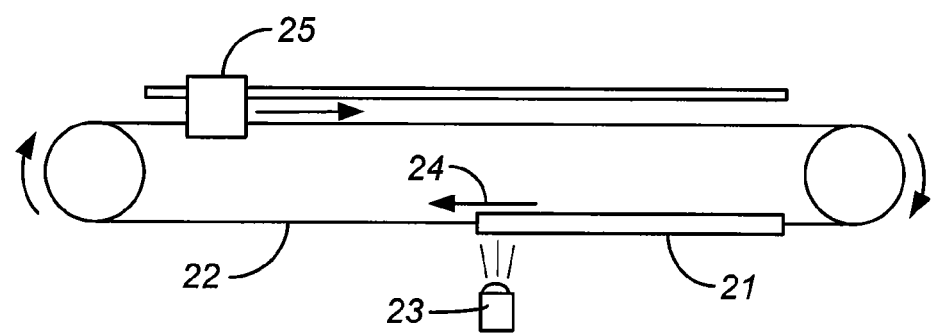
FIG. 2 is a side view of a second example of a scanning system in accordance with the present invention.

The embodiment of FIG. 2 is the reverse of the embodiment of FIG. 1. In FIG. 2, the planar target 21 is mounted to the belt 22 while the scanning head 23 is stationary. As the belt 22 rotates, the planar target 21 is drawn in the direction of the arrow 24 over the scanning head 23. The counterweight 25 moves at the same speed as the planar target 21 but in the opposite direction. This arrangement is useful for targets such as glass slides or other small supports with the sample arrays fixed in position, such as a film, on the support surface. In both of the embodiments of FIGS. 1 and 2, a two-dimensional array of sites on a target can be scanned by moving the entire system of pulleys, belts, scan head and counterweight in a direction transverse to the belt(s) in stepwise manner after each linear sweep of the scanning head to scan a series of rows in succession.

Figure 3:
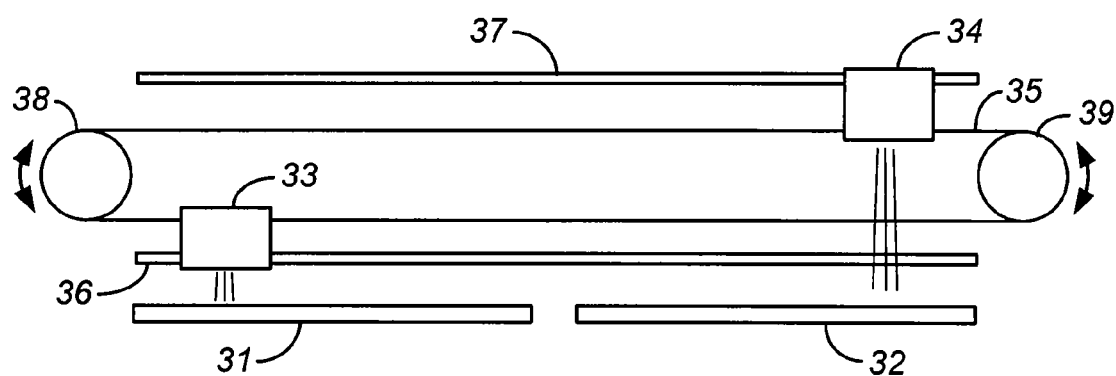
FIG. 3 is a side view of a third example of a scanning system in accordance with the present invention.

In the embodiment of FIG. 3, two targets 31, 32 are scanned, each by a separate scanning head 33, 34, respectively. Each scanning head 33, 34 serves as a counterweight to the other. Although not shown in the drawing, the belt 35 is a double-strand belt, and the rail 36 supporting one scanning head 33 and the rail 37 supporting the other scanning head 34 are both double rails, all with open spaces between that allow the upper scanning head 34 full access to its target 32. With both scanning heads on the same belt 35 and the scanning heads positioned on the belt such that the two scanning heads are never on the same side of the pulleys 38, 39, the movement of any one scanning head will only occur when the other is moving in the opposite direction, with the same effect as that achieved in the arrangement of FIG. 1. In a variation, the arrangement of FIG. 3 can be used with a single target, with the two scan heads alternately scanning the length of the target in opposite directions. Here again, the entire scanning apparatus can be moved in the direction perpendicular to the plane of the figure between each sweep of the scanning heads to scan a series of rows in succession. As a further variation, two different scanning heads can be used, each scanning the same entire row of sites on the target, the two scanning heads collecting different information from each site, thereby increasing the amount of information obtained by a single rotation of the belt.

Figure 4:
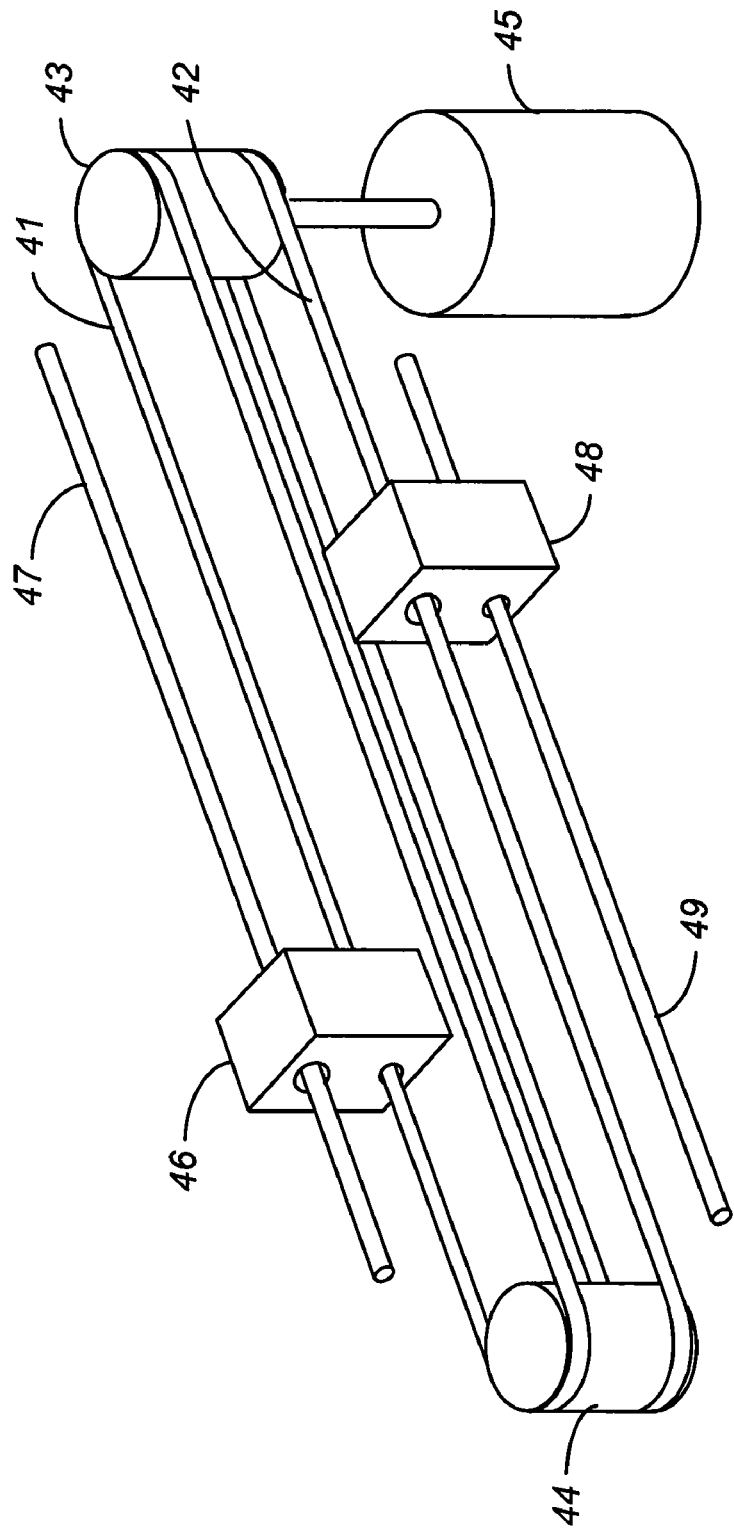
FIG. 4 is a perspective view of a fourth example of a scanning system in accordance with the present invention.

FIG. 4 shows a still further embodiment, this time employing two belts 41, 42 driven by a common pulley system, the pulley system consisting of a single timing pulley 43 and a single idler pulley 44, the timing pulley driven by a motor 45, which can be an ac or dc motor or a stepper motor. The scanning head 46 is secured to one of the belts 41 and slides along a guide rail 47, while the counterweight 48 is secured to the other belt 42 and slides along a second guide rail 49. With both belts operated by the same pulley system and the scanning head and counterweight sufficiently spaced apart, the scanning head and the counterweight will always move in opposite directions. In this arrangement and others as well, the guide rail 49 for the counterweight 48 can be eliminated without a significant loss in the balancing effect.

Figure 5:
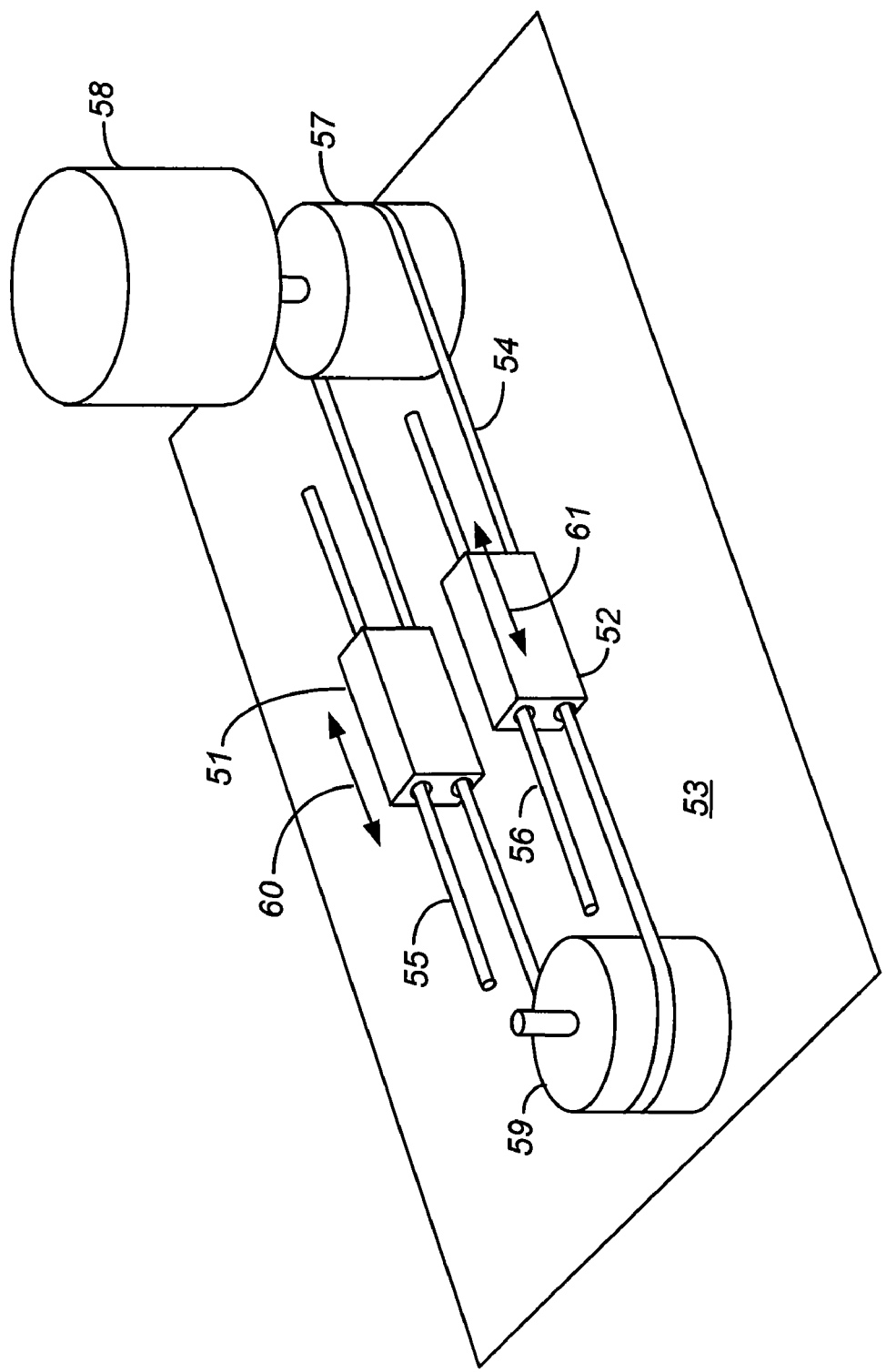
FIG. 5 is a perspective view of a fifth example of a scanning system in accordance with the present invention.

In the arrangement shown in FIG. 5, the scanning head 51 and counterweight 52, which is shown here as a second scanning head, travel in a common plane above the target plane 53. The scanning heads are mounted to the same belt 54 and separate guide rails 55, 56 are included for the two scanning heads. A timing pulley 57 is driven by a motor 58, and an idler pulley 59 is included, as in the embodiments of the preceding Figures. The two scanning heads move in the directions indicated by the arrows 60, 61, and are spaced along the belt to assure that they move in opposite directions.

In general, the path of travel of the counterweight will define its own center of gravity, and for best results, this center of gravity will be as close as possible to the center of gravity defined by the travel of the scanning head to minimize the reaction torque due to moving masses. Also in general for all embodiments, the counterweight will be more effective the closer its mass is to the mass of the scanning head, but a mass that is approximately equal to, rather than exactly equal to, that of the scanning head with also suffice. Preferably the mass of the counterweight is within about 10%, and preferably within about 5%, of that of the scanning head. When the counterweight is other than a scanning head itself, the counterweight can be any solid mass, molded, cut, cast or otherwise manufactured.

This invention is of value in instrumentation for real-time PCR (polymerase chain reaction), as well as any application when a rapidly moving scanning with high positional accuracy is needed. Examples of such applications are the scanning of microdot arrays on glass slides, microtiter plates, and microfluidic devices, i.e., devices with reservoirs connected by a network of fluidic channels of very small diameters.

While the foregoing description describes various alternatives to the components shown in the Figures, still further alternatives will be apparent to those who are skilled in the art and are within the scope of the invention.

The term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. A scanning system for scanning a planar target, in which said planar target and a scanning head are defined as members of a scanning pair, said scanning system comprising:
   a pair of continuous belts to which are mounted (i) one member of said scanning pair defined as a mobile scanning pair member mounted to one of said belts and (ii) a counterweight mounted to the other of said belts at locations whereby rotation of said belt means produces synchronous motion of said mobile scanning pair member and said counterweight in opposite directions along linear paths of motion parallel to and on a common side of the other member of said scanning pair, defined as a stationary scanning pair member; and
   drive means for rotating said belt means to produce said synchronous motion, said drive means comprised of a single timing pulley engaging both belts and a single idler pulley engaging both belts.

2. A scanning system for scanning a planar target, in which said planar target and a scanning head are defined as members of a scanning pair, said scanning system comprising:
   belt means to which are mounted (i) one member of said scanning pair defined as a mobile scanning pair member and (ii) a counterweight at locations whereby rotation of said belt means produces synchronous motion of said mobile scanning pair member and said counterweight in opposite directions along linear paths of motion parallel to and on a common side of the other member of said scanning pair, defined as a stationary scanning pair member, and wherein said linear path of motion of said mobile scanning pair member is between said linear path of motion of said counterweight and said stationary scanning pair member; and
   drive means for rotating said belt means to produce said synchronous motion.

3. A scanning system for scanning a planar target, said scanning system comprising:
   belt means to which are mounted (i) a first scanning head and (ii) a second scanning head at locations whereby rotation of said belt means produces synchronous motion of said first scanning head and said second scanning head in opposite directions along linear paths of motion parallel to, and on a common side of a first planar target; wherein said first scanning head is positioned to scan said first planar target, and said second scanning head is positioned to scan a second planar target, and
   drive means for rotating said belt means to produce said synchronous motion.

4. A scanning system for scanning a PCR plate, in which said PCR plate and a scanning head are defined as members of a scanning pair, said scanning system comprising:
   belt means to which are mounted (i) one member of said scanning pair defined as a mobile scanning pair member and (ii) a counterweight at locations whereby rotation of said belt means produces synchronous motion of said mobile scanning pair member and said counterweight in opposite directions along linear paths of motion parallel to and on a common side of the other member of said scanning pair, defined as a stationary scanning pair member; and
   drive means for rotating said belt means to produce said synchronous motion.

5. A scanning system for scanning a microarray of biological species, in which said microarray and a scanning head are defined as members of a scanning pair, said scanning system comprising:
   belt means to which are mounted (i) one member of said scanning pair defined as a mobile scanning pair member and (ii) a counterweight at locations whereby rotation of said belt means produces synchronous motion of said mobile scanning pair member and said counterweight in opposite directions along linear paths of motion parallel to and on a common side of the other member of said scanning pair, defined as a stationary scanning pair member; and
   drive means for rotating said belt means to produce said synchronous motion.

6. A scanning system for scanning a microfluidic device, in which said microfluidic device and a scanning head are defined as members of a scanning pair, said scanning system comprising:
   belt means to which are mounted (i) one member of said scanning pair defined as a mobile scanning pair member and (ii) a counterweight at locations whereby rotation of said belt means produces synchronous motion of said mobile scanning pair member and said counterweight in opposite directions along linear paths of motion parallel to and on a common side of the other member of said scanning pair, defined as a stationary scanning pair member; and
   drive means for rotating said belt means to produce said synchronous motion.

7. A method for scanning a planar target with a scanning head wherein said planar target and said scanning head are defined as members of a scanning pair, said method comprising:
   (a) with one member of said scanning pair mounted to one continuous belt of a pair of continuous belts and designated a mobile scanning pair member, designating the other member of said scanning pair a stationary scanning pair member and placing said stationary scanning pair member within scanning distance of said mobile scanning pair member; and
   (b) with a counterweight mounted to the other continuous belt of said pair of continuous belts at a location relative to said mobile scanning member such that rotation of said pair of continuous belts by a common drive means produces synchronous motion of said mobile scanning member and said counterweight in opposite directions, rotating said pair of continuous belts by said common drive means to cause said mobile scanning member to traverse said stationary scanning member while retaining said mobile scanning member and said counterweight on a common side of said stationary scanning member.

8. A method for simultaneously scanning a first planar target with a first scanning head and a second planar target with a second scanning head, said method comprising:
   (a) with said first scanning head mounted to belt means, placing said first planar target within scanning distance of said first scanning head;
   (b) with said second scanning head mounted to said belt means at a location relative to said first scanning head such that rotation of said belt means produces synchronous motion of said first and second scanning heads in opposite directions. placing said second planar target within scanning distance of said second scanning head; and
   (c) rotating said belt means to cause said first scanning head to traverse said first planar target and said second scanning head to traverse a second planar target.

9. A method for scanning a PCR plate with a scanning head wherein said PCR plate and said scanning head are defined as members of a scanning pair, said method comprising:
   (a) with one member of said scanning pair mounted to belt means and designated a mobile scanning pair member, designating the other member of said scanning pair a stationary scanning pair member and placing said stationary scanning pair member within scanning distance of said mobile scanning pair member; and
   (b) with a counterweight further mounted to said belt means at a location relative to said mobile scanning member such that rotation of said belt means produces synchronous motion of said mobile scanning member and said counterweight in opposite directions, rotating said belt means to cause said mobile scanning member to traverse said stationary scanning member while retaining said mobile scanning member and said counterweight on a common side of said stationary scanning member.

10. A method for scanning a microarray of biological species with a scanning head wherein said microarray and said scanning head are defined as members of a scanning pair, said method comprising:
   (a) with one member of said scanning pair mounted to belt means and designated a mobile scanning pair member, designating the other member of said scanning pair a stationary scanning pair member and placing said stationary scanning pair member within scanning distance of said mobile scanning pair member; and
   (b) with a counterweight further mounted to said belt means at a location relative to said mobile scanning member such that rotation of said belt means produces synchronous motion of said mobile scanning member and said counterweight in opposite directions, rotating said belt means to cause said mobile scanning member to traverse said stationary scanning member while retaining said mobile scanning member and said counterweight on a common side of said stationary scanning member.

11. A method for scanning a microfluidic device with a scanning head wherein said microfluidic device and said scanning head are defined as members of a scanning pair, said method comprising:
   (a) with one member of said scanning pair mounted to belt means and designated a mobile scanning pair member, designating the other member of said scanning pair a stationary scanning pair member and placing said stationary scanning pair member within scanning distance of said mobile scanning pair member; and
   (b) with a counterweight further mounted to said belt means at a location relative to said mobile scanning member such that rotation of said belt means produces synchronous motion of said mobile scanning member and said counterweight in opposite directions, rotating said belt means to cause said mobile scanning member to traverse said stationary scanning member while retaining said mobile scanning member and said counterweight on a common side of said stationary scanning member.

* * * * *